United States Patent [19]

Barfurth et al.

[11] Patent Number: 4,609,745

[45] Date of Patent: Sep. 2, 1986

[54] WATER-SOLUBLE ZIRCONIC ACID ESTERS

[75] Inventors: Dieter Barfurth, Troisdorf-Spich; Heinz Nestler, Troisdorf Eschmar, both of Fed. Rep. of Germany

[73] Assignee: Dynamit Nobel AG, Cologne, Fed. Rep. of Germany

[21] Appl. No.: 696,021

[22] Filed: Jan. 29, 1985

[30] Foreign Application Priority Data

Feb. 11, 1984 [DE] Fed. Rep. of Germany ....... 3404949

[51] Int. Cl.$^4$ ................................................ C07F 7/00
[52] U.S. Cl. ......................................... 556/40; 520/1; 106/220
[58] Field of Search .......................................... 556/40

[56] References Cited

U.S. PATENT DOCUMENTS 2,824,114  2/1958  Bostwick .
3,474,069  10/1969  Thomas .
4,478,755  10/1984  Robbins .

*Primary Examiner*—Helen M. S. Sneed
*Attorney, Agent, or Firm*—Felfe & Lynch

[57] ABSTRACT

Disclosed are new zirconic acid esters which contain glycol ether moieties as the ester grouping, and which are chelated with one and up to a maximum of two moles of acetylacetone. The new compounds can also contain up to a maximum of two moles of ester groupings of low alkanols. The new partially chelated zirconic acid esters are characterized by good solubility in water, in which they do not decompose at room temperature. Accordingly, they can also be used in aqueous systems as crosslinking agents or reaction accelerators.

6 Claims, No Drawings

WATER-SOLUBLE ZIRCONIC ACID ESTERS

BACKGROUND OF THE INVENTION

The subject matter of the present invention is zirconic acid esters which are stable and soluble in water without decomposition.

Organic derivatives of zirconic acid $Zr(OH)_4$ are very useful, reactive chemicals. Particularly important representatives of this group are tetraalkyl zirconates, such as for example tetrapropylzirconate and zirconic acid chelates, the most frequently used chelating agents being acetylacetone and triethanolamine. When these chelating agents are used, however, chelates are obtained which are very poorly soluble in any of the common solvents, or they lead to alkalinely reacting compounds.

These known zirconic acid esters and chelates are used as catalysts for polymerization, polyaddition and esterification and transesterification reactions, as crosslinking agents for polymeric substances such as organopolysiloxanes, nitrocellulose or resins containing hydroxyl groups, in the preparation of coatings, precision casting molds, textile finishing agents or water-repellentizing agents, and as an active agent for the surface treatment of glass. In any case, they are used in a water-free medium or water-free solvents, although the use of water is often desirable for economic and ecological reasons. The versatility of the zirconates as catalysts and crosslinking agents is based on the great reactivity of these compounds. At the same time, this reactivity always interferes with the use of these compounds when water is present in the reaction mixture. Alkyl zirconates even react with atmospheric moisture, so that dilutions with 96% pure alcohol already result in precipitation to zirconium hydroxide.

Attempts have therefore been made to stabilize these known zirconium compounds against the action of water. For example, it is proposed in German Federal Patent No. 22 04 531 to add to solutions of zirconium propylate or butylate such chelating agents as acetylacetone or acetic acid ester, hydroxycarboxylic acids, or polyvalent alcohols, leaving the alcohol that is split off, in addition to the 20 to 30% of the solvent alcohol originally present in the zirconate. The products thus obtained, however, are not pure compounds, but mixtures of the starting products with zirconium acetylacetonates or zirconium chelates of the other chelating agents in an alcoholic solution. If, for example, a mixture obtained in this manner with acetylacetone is concentrated by evaporation, a poorly soluble zirconium acetylacetonate then precipitates as a solid from this solution.

In a second method described in German Federal Patent No. 11 22 049, water-soluble metal alcoholates are obtained by reacting metal alcoholates of lower alcohols with special alcohols of longer chain length. These alcohols are obtained by adding ethylene oxide onto organic compounds having at least 4 carbon atoms and one active hydrogen atom. In the case of zirconium, compounds are thus formed which do hydrolyze after several hours of immersion in water, but their zirconium oxide content is greatly reduced; in the example of the zirconium tetraethylate mentioned therein it drops from 45.4% to 12.6%.

The problem therefore existed of finding zirconium esters of high zirconium oxide content which are liquid, which are soluble in water without the precipitation of insoluble hydrolyzates, and whose aqueous solutions have a neutral reaction.

THE INVENTION

As the solution to this problem, new zirconic esters having the following formula have been found:

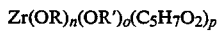

wherein:
R is an alkyl moiety of 1 to 8 carbon atoms,
R' is $-[A-O]_q-R$,
the moiety $C_5H_7O_2$ represents the acetyl acetone moiety, and
n is 0-2,
o is 1-3,
p is 1-2, on the condition that $n+o+p=4$, and
q is 1 to 8.

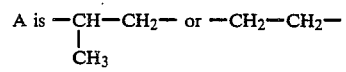

These new, partially chelated zirconic acid esters are liquid compounds at room temperature, and exhibit none of the disadvantages cited above. They need no solubilizers for the preparation of solutions and are miscible with water in any ratio without hydrolysis. Furthermore, they are reactive for the desired applications as above mentioned, and have a relatively high zirconium oxide content.

The zirconates of the invention are characterized by a content of at least one (poly-)glycol ether group, a content of no more than two acetylacetonyl groups, and saturation of any remaining valences of the zirconium atom with lower alkoxy groups. In particular, these are zirconates which have one acetylacetonyl group, one or two (poly-)glycol ether groups, and accordingly two or one low alkoxy group for each central zirconium atom.

The preparation of the zirconates of the invention can be performed in a manner known in itself through the esterification or transesterification of known zirconium compounds. It is best to start out with tetraalkyl zirconates which, for the sake of easy of handling, are obtainable commercially dissolved in an excess of the alcohol corresponding to the alkoxy group. In general, therefore, approximately 70 to 85% alcoholic solutions of the tetraalkyl zirconates are used as starting products.

In the actual practice of this preferred procedure, the zirconate is reacted in a suitable reaction vessel with the amounts of acetylacetone and glycolether corresponding to the desired composition of the end product, with the application of heat; the heat of reaction, or brief heating to a temperature slightly below the boiling point of the alcohol present, suffices for the performance of the reaction. Then both the alcohol originally present and the alcohol that has been formed by the reaction (one mole per mole of acetyl-acetone and glycolether) are distilled out, preferably in a vacuum at medium temperature.

If it is desired to perform the reaction in two steps, it is recommendable first to perform the reaction with the glycol ether, withdraw the alcohol present up to then in the reaction mixture, and then transpose with acetylacetone and again concentrate by evaporation. In case the alkyl zirconate is first made to react with acetylacetone, the danger exists, during the concentration, of an interim precipitation of solid acetylacetonates, which then, under certain circumstances, react with the glycol ether only with difficulty.

The expression, glycol ethers which can be used for the preparation of the new compounds, is to be understood to include both mono- and polyglycol ethers as well as (poly-) glycol ether esters corresponding to the general formula

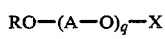

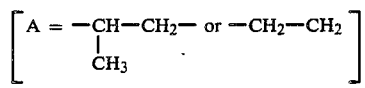

wherein R represents alkyl moieties of 1 to 8 carbon atoms, q values of 1 to 8, preferably 1 to 4, and X=H or

Examples of glycol ethers (X=H) are glycol monomethyl ether, glycol monoethyl ether, glycol monobutyl ether, diglycol monomethyl ether, diglycol monoethyl ether and diglycol monobutyl ether. The glycol ether esters

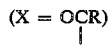

include, for example, glycol monomethyl ether acetate or diglycol monobutyl ether acetate. Generally these glycol ether esters are also called alkyl glycol carboxylates. When these glycol ether esters are put into the synthesis, their ester grouping reacts with a Zr-OR group with transesterification to a carboxylic acid ester and formation of the desired glycol ether grouping of the claimed compounds.

It is furthermore possible to bring mixtures of different glycol ethers or glycol ether esters and then to use directly the product obtained after distilling the alcohol, without separating it into its individual components.

The zirconium chelates of the invention are yellow-to-orange, more or less viscous liquids. They are soluble in water without hydrolysis. They can be used wherever zirconates are active as catalysts, crosslinking agents etc. These compounds find special use where other zirconates fail or even offer difficulties due to the presence of water or moisture, as additives in water varnish systems, as agents for crosslinking polyhydroxy compounds in water, as esterification catalysts, or in similar systems.

The following examples are intended to illustrate the preparation and the uses of the zirconium chelates of the invention, but the possible applications are not to be limited to the examples.

EXAMPLE 1

Preparation of
n-propoxy-bis-1-(2-(methoxyethoxy)-ethoxy-2,4-pentanedionato-zirconium 409.5 g of commercial propyl zirconate (0.9 mol of tetra-n-propoxy-zirconium in a 72% solution in 1-propanol) is weighed into the one-liter flask of a laboratory rotary vacuum evaporator, and first 216 g of methyldiglycol (1.8 mol, 2-(2-methoxyethoxy)ethanol) is added. Then 90 g of acetyl acetone (0.9 mol, 2,4-pentanedione) is stirred in portionwise, and the reaction product is heated at 80° C., with stirring, for 30 minutes. After cooling to 45° to 50° C., both the 1-propanol that was contained in the starting material and that which was formed by the reactions of the propyl zirconate with the methyl diglycol and the acetyl acetone are removed by distillation under reduced pressure (approx. 20–25 mbar). (Distillate yield: 272.5 g=approximately 98.5% of the theory). The product thus obtained is a yellow, viscous liquid with the following characteristics:

Refractive index $n_D^{20}$=1.5095−1.5110
Viscosity (20° C.)=6000−12000 mPa.s
Zirconium dioxide content=25.0−25.6%
Solubility:
  (a) in water: forms a clear 2.5% solution
  (b) in organic solvents: forms a clear 10% solution in isopropanol, methyl ethyl ketone, ethyl acetate, methylene chloride, toluene and heptane.

The above solutions are stable for at least 6 weeks at room temperature.

EXAMPLE 2

Preparation of
di-n-propoxy-2-(2-methoxyethoxy)-ethoxy-2,4-pentanedionato-zirconium 455 g of commercial propyl zirconate (1 mol tetra-n-propoxy-zirconium as a 72% solution in 1-propanol) is weighed into the one-liter flask of a laboratory rotary vacuum evaporator, and 120 g of methyldiglycol (1 mol, 2-(2-methoxyethoxy)-ethanol) and 100 g of acetyl acetone (1 mol, 2,4-pentanedione) are added successively. The reaction mixture thus obtained is freed of the 1-propanol that was formed by the reaction and that which was contained in the starting material, by distillation under reduced pressure (Distillate yield: 245.7 g: approximately 99.3% of theory).

The result is a yellow, viscous liquid with the following characteristics:

Refractive index $n_D^{20}$=1.5175−1.5195
Viscosity (20° C.)=1100−1600 mPa.s
Zirconium dioxide content=28.5−29.1%
Solubility:
  (a) in water: forms a clear 2.5% solution (b) in organic solvents: forms clear 10% solutions in isopropanol, methyl ethyl ketone, ethyl acetate, methylene chloride, toluene and heptane.

EXAMPLE 3

Preparation of butoxy-bis-2-(2-methoxyethoxy)ethoxy-2,4-pentanedionato-zirconium 409.5 g of commercial butyl zirconate (0.9 mol of tetra-n-butoxy-zirconium as an 84% solution in 1-butanol) is weighed into the one-liter flask of a laboratory rotary vacuum evaporator and 216 g of methyl diglycol (1.8 mol, 2-(2-methoxyethoxy)-ethanol) and 90 g of acetyl acetone (0.9 mol, 2,4-pentanedione) are successively added. This mixture is heated at 50° C. and then freed in vacuo of the 1-butanol contained therein, which originates from the reaction of the butyl zirconate with methyl diglycol and acetyl acetone, and from the starting butyl zirconate. The separation of the 1-butanol is performed at 20 to 25 mbar and a maximum water bath temperature of 80° C. (Distillate yield: 264.0 g=approximately 99.5% of the theory.) The product thus obtained is a viscous, orange liquid of the following characteristics:

Refractive index $n_D^{20}$=1.5080−1.5110
Viscosity (20° C.)=600−850 mPa.s
Zirconium dioxide content=24.5−25.2%
Solubility:
 (a) in water: forms a clear 2.5% solution
 (b) in organic solvents: forms a clear 10% solution in isopropanol, methyl ethyl ketone, ethyl acetate, methylene chloride, toluene and heptane.

These solutions are stable at room temperature for at least 6 weeks.

EXAMPLE 4

Preparation of n-propoxy-bis-(2-ethoxyethoxy)-2,4-pentanedionato-zirconium 455 g of commercial propyl zirconate (1 mol tetra-n-propoxy-zirconium as a 72% solution in n-propanol) is weighed into the one-liter flask of a laboratory rotary vacuum evaporator, and 180 g of ethyl glycol (2-ethoxyethanol) is added. This mixture is heated at 40° C. and with the application of a vacuum (20 to 25 mbar) it is freed of about 75% of the n-propanol it contains. Then, 100 g of acetyl acetone (1 mol, 2,4-pentanedione) is added and the mixture is heated at 50° C. Then, by a vacuum, this reaction mixture is freed of all of the volatile components in the form of n-propanol, the temperature being raised to 80° C. Distillate yield (steps 1+2): 304.0 g=98.9% of the theory.

The product thus obtained is an orange-red, viscous liquid with the following characteristics:

Refractive index $n_D^{20}$=1.5085−1.5105
Viscosity (20° C.)=7500−10000 mPa.s
Zirconium dioxide content=28.6−29.3%
Solubility:
 (a) in water: forms clear 2.5% solution
 (b) in organic solvents: forms clear 10% solution in isopropanol, methyl ethyl ketone, ethyl acetate, methylene chloride, toluene and heptane.

EXAMPLE 5

Use of the product of Example 2 as esterification catalyst in the preparation of a polyester from 1,4-butanediol and adipic acid 146 g (1 mol) of adipic acid and 99.4 g (1.1 mol) of 1,4-butanediol are weighed into an esterification apparatus provided with stirrer, thermometer, water separator and reflux condenser, and heated until the components dissolve to form a uniform mixture. At this temperature (about 150° C.), 0.15 g of the product of Example 2 is added and the mixture is heated until water begins to form at about 170° to 180° C. After 25 minutes, 70% of the theoretical amount of water has been produced, and to complete the esterification the mixture is treated at 200° C. for 2 hours in vacuo. The polyester thus obtained has an acid number of 5.6 and is clear in the molten state. In the case of a polyester prepared with 0.15 g of isopropyl titanate as catalyst for comparison, it takes 75 minutes for 70% of the theoretical amount of water to form. This latter polyester is obtained with an acid number of 5.0 after 2 hours of continued condensation, but in the molten state it is decidedly turbid.

EXAMPLE 6

Use of the product of Example 2 as a component of water-base adhesivizing primer Strips of a commercial, untreated polyethylene terephthalate film are immersed for 30 seconds in a 1% aqueous solution of the product described in Example 2, then dried for 30 minutes in air and 60 minutes in the convection drying oven, and then coated with a test varnish which contains about 20% solids and is pigmented with a little titanium dioxide, in a wet coat thickness of about 0.04 mm. After air drying overnight, and treatment in a convection drying oven (3 hours, 60° C.), they are tested for adhesion to the film by the adhesive-film peeling test. It was found that varnishes containing nitrocellulose (both ester-soluble and alcohol-soluble types), cellulose propionate or cellulose acetobutyrate as binding agents, on films treated in this manner, are not peeled off by the Tesafilm, while these varnishes, applied to untreated films, are completely pulled off in this test.

It will be understood that the specification and examples are illustrative but not limitative of the present invention and that other embodiments within the spirit and scope of the invention will suggest themselves to those skilled in the art.

We claim:

1. A zirconic acid ester of the formula

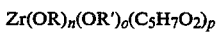

wherein:
R is an alkyl moiety of 1 to 8 carbon atoms,
R' is —[A"—O]$_q$—R,

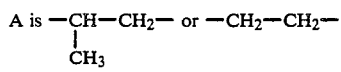

the moiety $C_5H_7O_2$ represents the acetyl acetone moiety, and n is 0–2, o is 1–3, p is 1–2, on the condition that n+o+p=4, and q is 1 to 8.

2. The zirconic acid ester of claim 1 n-propoxy-bis-2-(2-methoxyethoxy)ethoxy-2,4-pentanedionato-zirconium.

3. The zirconic acid ester of claim 1 di-n-propoxy-2-(2-(methoxyethoxy)ethoxy-2,4-pentanedionato-zirconium.

4. The zirconic acid ester of claim 1 butoxy-bis-2-(2-methoxyethoxy)ethoxy-2,4-pentanedionato-zirconium.

5. The zirconic acid ester of claim 1 n-propoxy-bis-(2-ethoxyethoxy)-2,4-pentanedionato-zirconium.

6. A method for the preparation of zirconic acid esters of claim 1, comprising reacting zirconic acid esters of the formula $Zr(OR)_4$ with 1 to 3 mol of glycol ethers or glycol ether esters, and with up to 2 mol of acetyl acetone, and distilling out released alcohol.

* * * * *

UNITED STATES PATENT AND TRADEMARK OFFICE
CERTIFICATE OF CORRECTION

PATENT NO. : 4,609,745

DATED : September 2, 1986

INVENTOR(S) : Dieter Barfurth

It is certified that error appears in the above-identified patent and that said Letters Patent is hereby corrected as shown below:

Column 4, line 11, "bis-1-(2-" should read --bis-2-(2- --.

Signed and Sealed this

Fourth Day of September, 1990

Attest:

HARRY F. MANBECK, JR.

Attesting Officer

Commissioner of Patents and Trademarks